United States Patent
Sasagawa

(10) Patent No.: US 7,156,657 B2
(45) Date of Patent: Jan. 2, 2007

(54) DENTAL ARTICULATOR, METHOD FOR PRODUCING DENTURES AND METHOD FOR ADJUSTING THE ARTICULATOR IN OCCLUSION HEIGHT IN PREPARING THE DENTURES

(76) Inventor: Osamu Sasagawa, A 202, 43 Aza Karigaya Marumori-machi, Igu-gun, Miyagi 981-2100 (JP)

( * ) Notice: Subject to any disclaimer, the term of this patent is extended or adjusted under 35 U.S.C. 154(b) by 107 days.

(21) Appl. No.: 10/669,637

(22) Filed: Sep. 25, 2003

(65) Prior Publication Data

US 2004/0131991 A1 Jul. 8, 2004

(30) Foreign Application Priority Data

Sep. 25, 2002 (JP) ............................. 2002-280015

(51) Int. Cl.
*A61C 11/00* (2006.01)
(52) U.S. Cl. .......................................... 433/60; 433/54
(58) Field of Classification Search ................. 433/54, 433/56, 59, 60, 65
See application file for complete search history.

(56) References Cited

U.S. PATENT DOCUMENTS

| | | | | | |
|---|---|---|---|---|---|
| 1,736,006 | A | * | 11/1929 | Hagman | 433/60 |
| 4,163,320 | A | * | 8/1979 | Yokota | 433/60 |
| 5,967,776 | A | * | 10/1999 | Kim | 433/60 |

* cited by examiner

*Primary Examiner*—Cary E. O'Connor
(74) *Attorney, Agent, or Firm*—Rader, Fishman & Grauer PLLC

(57) ABSTRACT

Articulator (1), which may precisely reproduce the occlusion height in the mouth in preparing a denture excellent in occlusion properties and favorable to a patient, comprises: lower frame (23) provided with lower jaw model support (21) in its upper surface, detachably mounted on which support (21) is a lower jaw model (20); stand (30) mounted in a rear portion of the lower frame (23) to extend upright; upper frame (13) provided with an upper jaw model support (11) in its lower surface, detachably mounted on which support (11) is an upper jaw model (10); circular plates (40) which vary in thickness and are provided in each of the supports (11, 21), the circular plates (40) being selected so as to enable a jaw model mounting surface of each of the supports (11, 21) to be movable in parallel with each of the frames (13, 23).

4 Claims, 13 Drawing Sheets

DENTAL ARTICULATOR, METHOD FOR PRODUCING DENTURES AND METHOD FOR ADJUSTING THE ARTICULATOR IN OCCLUSION HEIGHT IN PREPARING THE DENTURES

BACKGROUND OF THE INVENTION

1. Field of the Invention

The present invention relates to a dental articulator used in preparing a new denture from an existing denture. More particularly, the present invention relates to the structure of a dental articulator capable of preparing the new denture from the existing denture on the basis of features of a patient's jaw joint which is wide in allowance in relative movement between a lower jaw and an upper jaw of the patient, wherein the new denture is free from any feeling of physical disorder even when it is new for the patient, wherein the dental articulator may reproduce the patient's dental arches in the patient's oral cavity, wherein the dental arches are precise in occlusion height in the oral cavity defined between the lower and the upper jaw and heretofore neatly fit to the patient in use. Further, the present invention relates to both a method for producing a new denture and a method for adjusting the occlusion height of the dental articulator in preparing the new denture from the existing denture.

2. Description of the Related Art

As shown in FIG. 16, a conventional dental articulator 1 (for example, such as one disclosed in Japanese Patent application Laid-Open No. Hei 9-206315) comprises: an upper frame 13 provided with an upper jaw model supporting portion 11 which is formed in a so-called "Frankfort plane", mounted on which supporting portion 11 is an upper jaw model 10; a lower frame 23 provided with both a lower jaw model supporting portion 21 and a front end portion on which an incisal table 22 is mounted, mounted on which supporting portion 21 is a lower jaw model 20; a stand portion 30 for supporting both the upper frame 13 and the lower frame 23 in a manner such that a distance between the upper frame 13 and the lower frame 23 is adjustable by adjusting these frames 13, 23 independently of one other in position, which distance is hereinafter referred to as "occlusion height"; and, an incisal pin 14 which is mounted on the upper frame 13 so as to have its lower end portion disposed adjacent to an upper surface of the incisal table 22.

In the conventional dental articulator 1 having the above construction, the upper jaw model supporting portion 11 and the lower jaw model supporting portion 21 are detachably mounted on the upper frame 13 and the lower frame 23, respectively.

On the other hand, the dentures thus prepared become worn during daily mastication of meals. Consequently, it is necessary for the patient to replace the thus worn dentures with new ones every few years.

In preparing a new denture based on the patient's existing (i.e., old or worn) denture 50 by using the dental articulator 1, an old upper denture 51 has its border (i.e., peripheral portion) extended upward (as viewed in FIG. 1) to form a dam by the addition of is compound material. Then, the old upper denture 51 provided with the dam in its border is returned to the patient oral cavity, so that the dam of the old upper denture 51 is brought into contact with the mucous membrane of the patient's oral cavity and deformed by the pressure of the membrane to become neatly fit to the patient's oral cavity. Hereinafter, a process step for forming and modifying in shape the dam of the modified old denture is referred to as a "dam formation" step. The old upper denture 51 having been subjected to the "dam formation" step is then used as an upper dental tray 51. In use, the upper dental tray 51 thus prepared has its entire tissue side loaded with an impression material in order to obtain the impression of a mucous membrane of the patient's oral cavity when returned into the patient mouth. Likewise, an old lower denture 52 is modified in shape in a manner similar to the modification of the old upper denture 51 to become a modified old lower denture 52 capable of serving as a lower dental tray 52, as viewed in FIG. 1.

After the impression material loaded on the tissue side of the modified old upper denture 51 (which serves as the upper dental tray) has set or hardened, gypsum is poured in an oral cavity side of the modified old upper denture 51 to take the impression of the teeth and gum of the old upper denture 51. After the gypsum has set or hardened, the hardened gypsum is taken out of the old upper denture 51 to become an upper negative gypsum model of the teeth and gum of the modified old upper denture 51. Likewise, a lower negative gypsum model of the teeth and gum of the modified old lower denture 52 is made in a manner similar to the making of the upper negative gypsum model.

After that, a paraffin wax is poured into the upper and the lower negative gypsum model to produce an upper and a lower wax positive model, respectively.

The wax positive models having been softened by heating are then inserted into the patient's oral cavity and subjected to a so-called "occlusion confirmation" process in which the wax positive models are corrected in shape in occlusion action. In the thus corrected wax positives, now, their wax teeth are replaced with pre-cast more rigid prosthetic teeth having been selected by the patient in type, size and shade, so that a so-called "occlusion bite pieces" are prepared. The occlusion bite pieces form pre-forms of the new dentures.

Added to the thus prepared pre-forms of the new dentures are gum portions to complete the pre-forms.

By using the thus completed pre-forms in a so-called "immersion process", negative molds of the new dentures are prepared. More specifically, the substitution of a suitable resin material for the wax gum portion of each of the completed pre-forms is carried out by a conventional lost wax process known in the art (see, Jun Nishiura, "dental technique for a denture with a base, general denture version", I-Shi-Yaku Shutzpan Kabushiki Kaisha, May 20, 1976, pp. 33–112).

Problems to be solved by the present invention will be now described.

In the conventional method for producing the new denture, however, there is no standard in occlusion height (i.e., precise height in occlusion) in the oral cavity in conducting the so-called "occlusion confirmation" process in which the wax positive models are corrected in shape during the occlusion action. Heretofore, the occlusion height is determined by individual dentist's experience. This leads to frequent modifications of the new dentures in shape after delivered to the patients.

In other words, in the oral cavity side of the new denture, it is possible to utilize the information obtained from the old denture as to a dam formed in a border portion of the new denture. In contrast with this, in the tissue side of the new denture, it is not possible to utilize any information obtained from the old denture as to the occlusion height in the patient's oral cavity. Further, since a new set of artificial teeth are embedded in the dental arch of the new denture, it is necessary for the patient to return many times for follow-up appointments in order to have the dentist reshape and reconfigure the new denture so that it seats properly in the patient's mouth and feels correct to the patient. Such multiple return visits to the dentist office are not only annoying to the paying customer (i.e., patient), but also cost the dentist time and money, reduce patient confidence in the dentist, and, occasionally, one losses the patient's patronage.

The old dentures are useful in preparing the new dentures since the old dentures have been used actually for a long period of time by the patient, and therefore have a plenty of helpful information as to the new dentures. Therefore, it is very important to utilize the information obtained from the old dentures in preparing the new ones.

As for the conventional dental articulator having the above construction, it is not possible for the conventional dental articulator to compensate for the amount of wear in the teeth portion of the old denture in setting the occlusion height in the patient's oral cavity between the upper jaw model and the lower jaw model. This makes it impossible to prepare the new dentures on the basis of the old dentures, particularly, their occlusion conditions. More particularly, in the conventional dental articulator, it is not possible to move the upper and the lower jaw model in parallel with each other when the incisal pin 14 is adjusted to compensate for the amount of wear of the old dentures. Further, the incisal pin 14 may adjust a distance between the upper and the lower jaw model in their front end portions only. Due to these facts, an occlusion height (i.e., distance between the front end portions of the jaw models) is different from another occlusion height (i.e., distance between the rear end portions of the same jaw models) in the same patient mouth. This leads to improper occlusion state in the patient's oral cavity.

Further, in the conventional dental articulator, by adjusting its stand portion 30 in length, it is possible to adjust in distance between the upper frame 13 and the lower frame 23. However, since the amount of wear of the upper jaw model 10 is often different from that of the lower jaw model 20, it is not possible to set a proper occlusion height even when the stand portion 30 is adjusted in length. Due to this, it is not possible for the conventional dental articulator to properly set each of the upper jaw model 10 and the lower jaw model 20, i.e., not possible to reproduce the actual occlusion conditions of the upper jaw model 10 and the lower jaw model in the patient's mouth.

In other word, in the conventional dental articulator, the jaw joint is realized in motion only by means of the incisal pin 14 as to the occlusion height in the patient's oral cavity. However, the jaw joint is different from any other joints since the jaw joint permits both the upper jaw and the lower jaw to move independently of one other in every direction by approximately 4 mm at maximum. Consequently, the teeth of the dentures are worm in mastication of everyday meals and therefore reduce in height. Due to this, the jaw joint loses its tightness. The inventor of the present invention has found the fact that the teeth of the dentures are substantially evenly worn in the same horizontal plate. This finding leads to the conclusion that: in preparing a new denture from an existing or old denture, since the conventional dental articulator can't conduct any balanced adjustment in occlusion height due to its utter lack of consideration regarding the jaw joint's freedom in motion, it is not possible to prepare any new denture excellent in occlusion state.

SUMMARY OF THE INVENTION

Under such circumstances, the present invention was made. Consequently, it is an object of the present invention to provide a dental articulator, a method for preparing a new denture from an existing denture and a method of adjusting the occlusion height, wherein the dental articulator is prepared in consideration of the features of the jaw joint, and permits the new denture to be excellent in occlusion condition, prepared in a short period of time and accurately reproduce the occlusion height in the patient's oral cavity.

In accordance with a first aspect of the present invention, the above object of the present invention is accomplished by providing:

A dental articulator comprising:

a lower frame (23) provided with a lower jaw model supporting portion (21) in its upper surface, wherein a lower jaw model (20) is detachably mounted on the supporting portion (21) through one of height-control means (16, 24, 40, 43);

a stand portion (30) disposed upright in a rear portion of the lower frame (23);

an upper frame (13) capable of performing its opening and closing motion relative to the stand portion (30), wherein the upper frame (13) is provided with an upper jaw model supporting portion (11) in its lower surface, wherein an upper jaw model (10) is detachably mounted on the supporting portion (11) through another one of the height-control means (16, 24, 40, 43);

wherein the height-control means (16, 24, 40, 43) enables the jaw model (10, 20) to be displaced vertically without any inclination relative to the frame (13, 23).

In the dental articulator having the above construction, preferably the height-control means (16, 24, 40, 43) is constructed of a plurality of circular planar stages (16, 24) which differ from each other in thickness and detachably mounted on the supporting portion (11, 21) to make it possible to displace the jaw model (10, 20) vertically without any inclination relative to the frame (13, 23) when a first one of the circular planar stages (24) is exchanged for another one different from the first one in thickness.

It is also preferable that the height-control means (16, 24, 40, 43) is constructed of a plurality of circular plates (40) each disposed between the supporting portion (11, 21) and the circular planar stage (24) and differs from each other in thickness to make it possible to displace the jaw model (10, 20) vertically without any inclination relative to the frame (13, 23) when a first one of the circular plates (40) is exchanged for another one having a thickness different from that of the first one.

It is also preferable that the height-control means (16, 24, 40, 43) is constructed of a calibrated cylinder (43), the calibrated cylinder (43) passing through a through-hole of the supporting portion (11, 21) to have its front end portion abut on the circular planar stage (16, 24) so that the circular planar stage (16, 24) is vertically displaced without any inclination relative to the supporting portion (11, 21) when the calibrated cylinder (43) is vertically slidably moved in the through-hole of the supporting portion (11, 21).

In the dental articulator having the above construction, preferably the calibrated cylinder (43) is provided with a vertical scale in its outer peripheral surface and a central threaded hole (44) in its central portion, which threaded hole (44) is threadably engaged with a treaded portion of a stop screw (17, 25), which threaded portion of the stop screw (17, 25) has its front end portion threadably engaged with a threaded hole (16a, 24a) of the circular planar stage (16, 24), wherein a lateral screw member (45) is threadably engaged with a threaded through-hole of a side portion of the frame (13, 23) to have its front end portion abut against a side peripheral portion of the calibrated cylinder (43) to fix the same (43) to the frame (13, 23) after the calibrated cylinder (43) is displaced by a desired amount relative to the frame (13, 23).

In accordance with a second aspect of the present invention, the above object of the present invention is accomplished by providing:

A method for producing a new denture on the basis of an existing denture (50) comprising an upper existing denture (51) and a lower existing denture (52) by using a dental articulator, wherein the new denture comprises an upper and a lower new denture, wherein the articulator is provided with a height-control means (16, 24, 40, 43) for control in height independently each of an upper jaw model supporting portion (11) of an upper frame (13) and a lower jaw model supporting portion (21) of a lower frame (23), wherein an upper jaw model (10) is detachably mounted on the upper jaw model supporting portion (11) of the upper frame (13) while a lower jaw model (20) is detachably mounted on the lower jaw model supporting portion (21) of the lower frame (23), the method comprising the steps of:

performing a myoplastic operation of the existing dentures (50), in which operation a compound material (61) is applied to each of patient's tissue contact sides of the existing dentures (50), wherein the existing dentures (50) carrying the compound material (61) having been applied thereto are then returned to a patient's oral cavity and modified in shape by the patient's oral cavity to fit the oral cavity;

applying an impression material (62) onto the compound material (61) which has been applied to each of the patient's tissue contact sides of the existing dentures (50) and modified thereby in shape, wherein an impression piece of each of the patient's tissue contact sides of the existing dentures (50) thus modified is obtained by means of the impression material (62);

measuring the impression piece (62) at a plurality of points thereof in thickness to calculate an average value of the thickness of the impression piece (62);

pouring a dental stone material (63) on an impression side of the impression piece (62) of the existing dentures (50) to permit the dental stone material (63) to be set or hardened so that a dental stone negative mold (63) of each of the impressed old dentures (50) is obtained with respect to each of the upper existing denture (51) and the lower existing denture (52);

mounting an occlusion planar plate (70) on the lower frame (23), wherein the upper existing denture (51) is temporarily fixed to an upper surface of the occlusion planar plate (70) and has its dental stone negative mold (63) bonded to a lower surface of the upper jaw model supporting portion (11) of the upper frame (13) through the height-control means (16, 24, 40, 43) by means of gypsum (60);

applying an impression paper (72) to an upper surface of the occlusion plate 70 so that an impression (73) of a dental arch of the upper existing denture (51) is printed on the impression paper (72);

removing the occlusion plate (70) is from the lower frame 23 so that the lower existing denture (52) is mated and combined with the upper existing denture (51) by using a fastening means (75), wherein the lower existing denture (52) thus combined with the upper existing denture (51) has its dental stone negative mold (63) bonded to an upper surface of the lower jaw model supporting portion (21) of the lower frame (23) through the height-control means (16, 24, 40, 43) by means of gypsum (60);

removing the upper existing denture (51) from its the dental stone negative mold (63) so that the upper jaw model (10) constructed of both the dental stone negative mold (63) and the gypsum (60) thus poured thereto is obtained;

removing the lower existing denture (52) from its the dental stone negative mold (63) so that the lower jaw model (20) constructed of both the dental stone negative mold (63) and the gypsum (60) thus poured thereto is obtained;

adjusting in height the supporting portion (11, 21) by using the height-control means (16, 24, 40, 43) with reference to the average value of the thickness of the impression piece (62) to control an occlusion height of the dental articulator;

removing the lower jaw model (20) from the supporting portion (21) on which the occlusion plate (70) is then mounted, wherein the occlusion plate (70) carries thereon the impression paper (72) having been printed with the dental arch of the upper existing denture (51);

pouring a paraffin wax into the upper jaw model (10) which forms an upper negative gypsum model to produce an upper wax positive model;

softening the upper wax positive model by heating, wherein the upper wax positive model having been thus softened is then inserted into the patient's oral cavity and subjected to an occlusion confirmation process in which the wax positive model is corrected in shape in occlusion action;

replacing wax teeth of the upper wax positive model thus corrected in shape with pre-cast more rigid prosthetic teeth with reference to the dental arch, wherein the prosthetic teeth have been selected by the patient in type, size and shade, so that an occlusion bite piece is prepared, the occlusion bite piece forming a pre-form of the upper new denture;

removing the occlusion plate (70) from the supporting portion (21) of the lower frame (23) so that the lower jaw model (20) is mounted on the supporting portion (21);

a paraffin wax into the lower jaw model (20) which forms a lower negative gypsum model to produce a lower wax positive model;

softening the lower wax positive model by heating, wherein the lower wax positive model having been thus softened is then inserted into the patient's oral cavity and subjected to an occlusion confirmation process in which the wax positive model is corrected in shape in occlusion action; and replacing wax teeth of the lower wax positive model thus corrected in shape with pre-cast more rigid prosthetic teeth with reference to the dental arch, wherein the prosthetic teeth have been selected by the patient in type, size and shade, so that an occlusion bite piece is prepared, the occlusion bite piece forming a pre-form of the lower new denture.

Preferably, the method described above further comprises the steps of;

obtaining a bite (55), which is a negative impression of the existing denture (50) in occlusion arrangement, the step of obtaining the bite (55) being followed by the step of performing the myoplastic operation of the existing dentures (50); and having the lower existing denture (52) abut on the upper existing denture (51) through the bite (55) thus obtained, wherein the lower existing denture (52) has its dental stone negative mold (63) bonded to an upper surface of the lower jaw model supporting portion (21) of the lower frame (23) by means of the gypsum (60).

According to the method of the present invention, it is possible to properly adjust the occlusion height by adjusting in lateral position both the upper and the lower jaw model independently of one other. Due to this, it is possible to determine each of the upper jaw model and the lower jaw model in lateral position on the basis of the corresponding occlusion height in the individual patient's oral cavity. This makes it possible to arrange the teeth of the new denture substantially in the same manner as that of the teeth of the existing denture. Due to this, it is possible for the new denture of the present invention to make the patient free from any feeling of physical disorder. Further, it is possible for the new denture of the present invention to utilize all the helpful information of the existing denture. Therefore, it is possible for the present invention to make the new denture excellent in fitness, with which the patient is satisfied.

BRIEF DESCRIPTION OF THE DRAWINGS

The above and other objects, advantages and features of the present invention will be more apparent from the following description taken in conjunction with the accompanying drawings in which.

DETAILED DESCRIPTION OF THE PREFERRED EMBODIMENTS

The best modes for carrying out the present invention will be described in detail using embodiments of the present invention with reference to the accompanying drawings.

Figure 1:
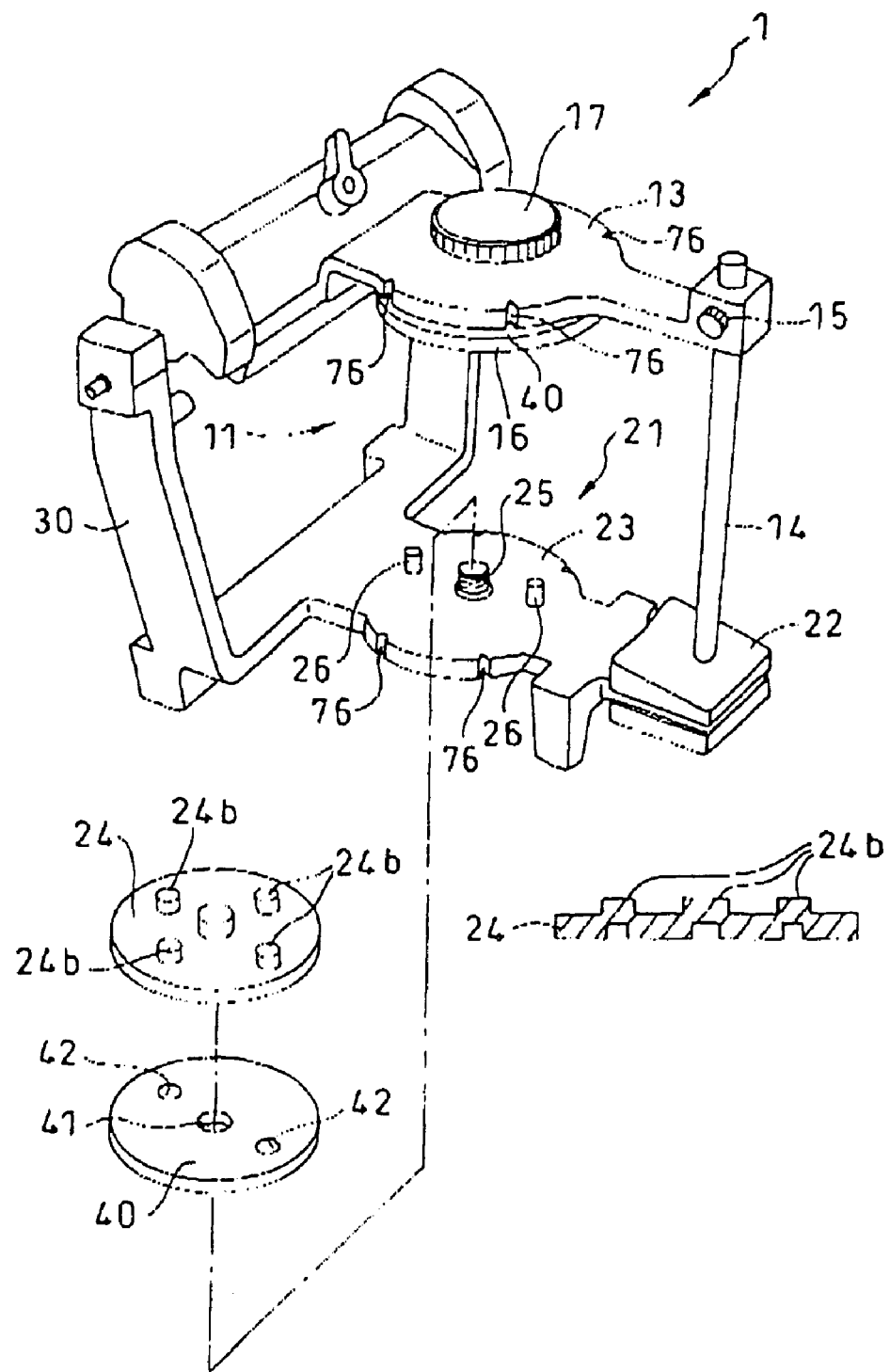
FIG. 1 is a perspective view of the first embodiment of the dental articulator of the present invention.
Figure 2:
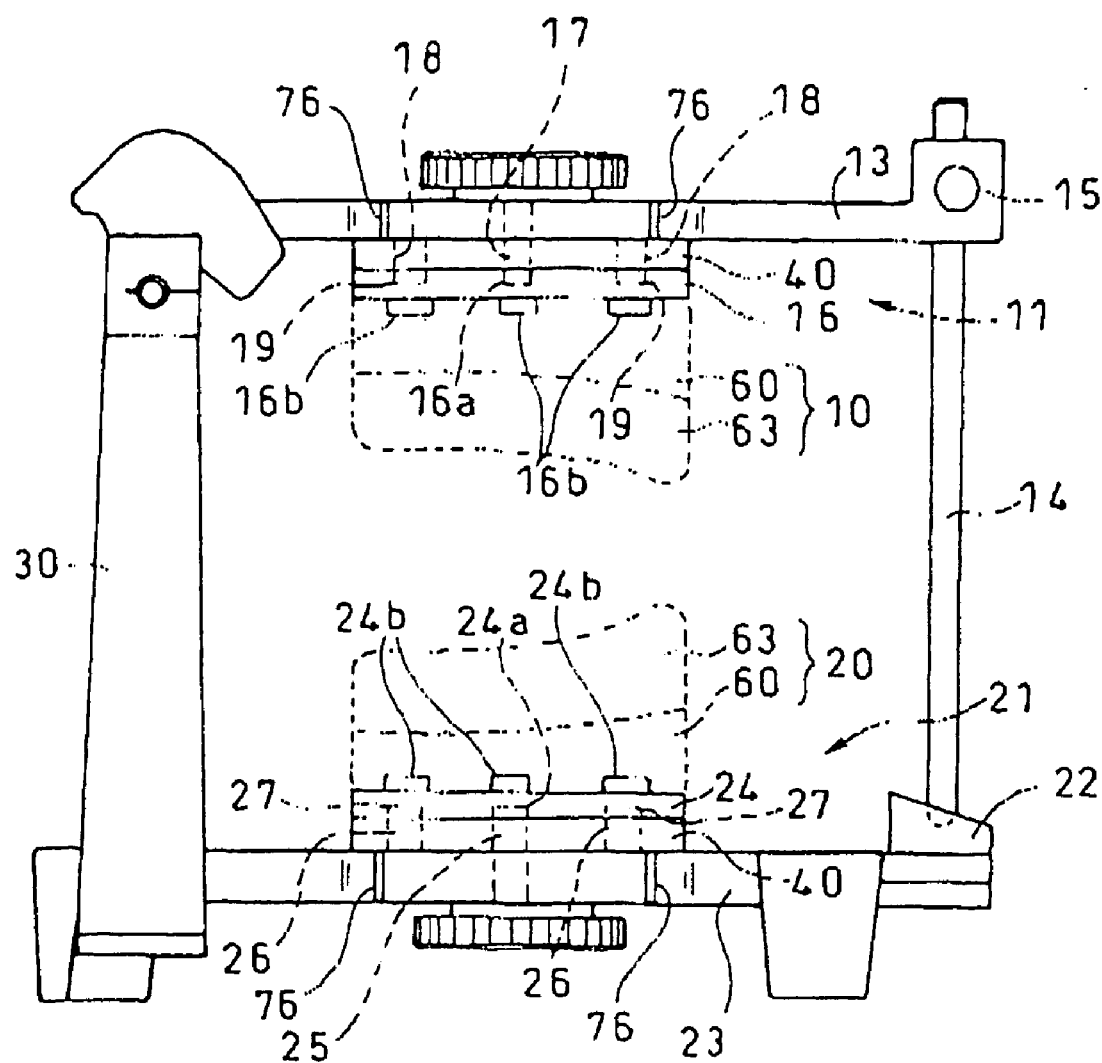
FIG. 2 is a side view of the dental articulator of the present invention shown in FIG. 1.

FIG. 1 shows a first embodiment of a dental articulator 1 of the present invention, a side view of which articulator 1 is shown in FIG. 2. The articulator 1 is provided with a plurality of circular plates 40 each forming a height-control means.

As shown in FIGS. 3(a) and 3(b), the circular plates 40 varies in thickness. More specifically, in this first embodiment, four different kinds of the planar plates 40 are employed.

In addition to these planar plates 40, the articulator 1 of the present invention comprises: a lower frame 23 provided with a lower jaw model supporting portion 21 in its upper surface, wherein a lower jaw model 20 is detachably mounted on an upper surface of the lower jaw model supporting portion 21 through a selected one of the circular plates 40; a pair of stand portions 30 both provided upright in a rear portion of the lower frame 23; and, an upper frame 13 provided with an upper jaw model supporting portion 11 in its lower surface, wherein the upper fame 13 is articulately connected to the stand portions 30, and an upper jaw model 10 is detachably mounted on a lower surface of the upper jaw model supporting portion 11 through a selected one of the circular plates 40.

As is clear from FIG. 1, each of the frames 13, 23 has a substantially T-shaped form as a whole, and the supporting portions 11, 21 thereof widened laterally and rounded in periphery.

On the other hand, an incisal pin 14 is slidably mounted in a front end portion of the upper frame 13 and fixed to the frame 13 by fastening a stop screw 15 provided therein. By loosening the stop screw 15, it is possible to adjust the incisal pin 14 in length between the under surface of the upper frame 13 and an upper surface of an incisal table 22, which is mounted on an upper surface of a front end portion of the lower frame 23 to abut against a lower end portion of the incisal pin 14 thus adjusted in length. Further, as will be described later in detail with respect the replacement of wax teeth of a modified existing denture with separate pre-cast artificial teeth, it is also possible to utterly dislodge the incisal pin 14 from the front end portion of the upper frame 13 in order to improve the articulator 1 in workability in the replacement of the wax teeth of the modified existing denture with the artificial teeth.

As shown in FIG. 2, the upper jaw model 10 and the lower jaw model 20 both described above are bonded to the upper jaw model supporting portion 11 and the lower jaw model supporting portion 21, respectively, by means of gypsum or like material. Such bonding process will described later in detail.

In the lower jaw model supporting portion 21, as shown in dotted lines, a stop screw 25 has its elongated threaded portion extended upward and thereby passed through a central portion of each of the lower jaw model supporting portion 21 and the circular plate in this order from the bottom of the supporting portion 21. As a result, the threaded portion of the stop screw 15 is threadably engaged with a threaded hole 24a of a circular planar stage or mounting plate 24. Consequently, it is possible to fixedly mount the mounting plate 24 on the lower jaw model supporting portion 21 through the circular plate 40 by fastening the stop screw 15. Provided in an upper surface of the lower frame 23 are a pair of upright projections 26 each having a circular shape in cross section. These projections 26 are detachably engaged with a pair of lower surface's blind holes 27 of the circular planar stage 24 in an insertion manner.

Figure 3:
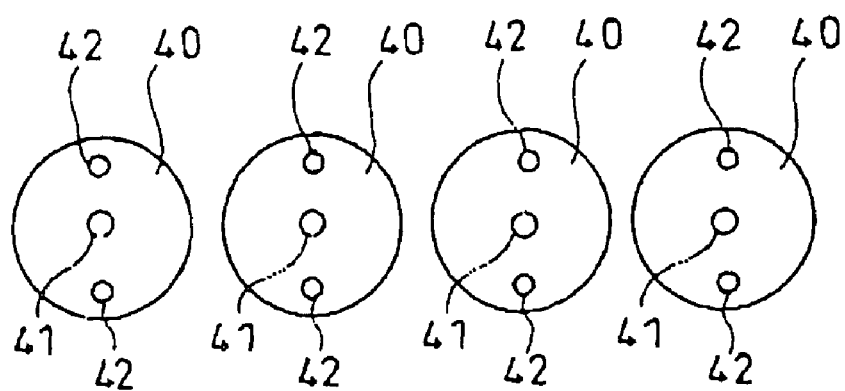
FIG. 3(a) is a plan view of a plurality of circular plates mounted on the dental articulator shown in FIG. 1.
FIG. 3(b) is a side view of the circular plates shown in FIG. 3(a)
Figure 3:
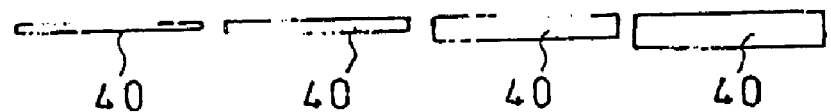

It is possible to adjust in height the circular planar stage 24 in the articulator 1 by selecting a desired one of the circular plates 40 shown in FIGS. 3(a) and 3 (b), wherein the thus selected one 40 is disposed between the circular planar stage 24 and the lower jaw model supporting portion 21 to set the height of the circular planar stage 24 at a desired level in the articulator 1. In other words, the lower jaw model supporting portion 21 provides a means for moving the lower jaw model 20 without inclining the model 20. More specifically, such means is essentially constructed of a plurality of different kinds of the circular plates 40 different from each other in thickness, as shown in FIG. 3(b). For example, a first one of the circular plates 40 may have a thickness of 0.5 mm; a second a thickness of 1.0 mm; a third a thickness of 2.0 mm; and, a fourth may have a thickness of 3.0 mm. Each of the circular plates 40 is provided with a central through-hole 41 its central portion, which through-hole 41 is passed through by the threaded portion of the stop screw 25. Therefore, as described above, it is possible to adjust the height of the lower jaw model supporting portion 21 (more specifically, an upper surface of the circular planer stage 24) by selecting a desired one among the circular plates 40.

Further, each of the circular plates 40 is provided with a pair of diametrically opposed through-holes 42, which serve as means for stabilizing the circular plate 40 when these through-holes 42 receive therein the corresponding projections 26 of the lower frame 23. It is clear that the thus engaged projections 26 of the lower frame 23 may prevent the corresponding circular plate 40 from rotating relative to the lower frame 23.

A similar means for moving the upper jaw model 10 without inclining the model 10 is also provided in the upper fame 13, and therefore has substantially the same construction as that of the means provided in the lower frame 23 just described in the above. In other words, in the upper jaw model supporting portion 11, such means is essentially constructed of a plurality of different kinds of the circular plates 40 different from each other in thickness, as shown in FIG. 3(b). Each of the circular plates 40 is provided with the central through-hole 41 in its central portion, which through-hole 41 is passed through by a threaded portion of a stop screw 17. Therefore, it is possible to adjust the height of the upper jaw model supporting portion 11 (more specifically, a lower surface of a circular planer stage 16) by selecting a desired one among the circular plates 40. As for the circular planer stage 16, this stage 16 is provided with a threaded blind hole 16a in its upper surface, as shown in dotted lines in FIG. 2. Threadably engaged with this threaded blind hole 16a is the threaded portion of the stop screw 17, which has the threaded portion thereof passed through both the upper frame 13 and the circular plate 40 from upside in this order and threadably engaged with the threaded blind hole 16a of the circular planar stage 16. Consequently, it is possible to fixedly mount the circular planar stage 16 on the upper frame 13 through the circular plate 40 by fastening the stop screw 17 provided in a lower surface of the upper frame 13 is a pair of upright projections 18 capable of being received in a pair of hole portions 19 of the circular planar stage 16. The height of this circular planar stage 16 is adjusted by inserting a desired one of the circular plates 40 between the circular planar stage 16 and the lower surface of the upper frame 13, which desired one has a desired thickness to adjust the height of the circular planar stage 16.

Further, each of the circular plates 40 is provided with a pair of diametrically opposed through-holes 42, which serve as means for stabilizing the circular plate 40 when these through-holes 42 receive therein the corresponding upright projections 18 of the upper frame 13. It is clear that the thus engaged projections 18 of the upper frame 13 may prevent the corresponding circular plate 40 from rotating relative to the upper frame 13. As is clear from FIG. 2, the selected one of the circular plates 40 is interposed between the circular planer stage 16 and the lower surface of the upper frame 13.

On the other hand, the circular planar stages 16 and 24 are provided with a plurality of convex portions 16b and 24b in their exposed sides, respectively. Each of these convex portions 16b and 24b serves as a better connection means for gypsum, which will be described later.

Further, as already described above, the upper frame 13 and the lower frame 23 are provided with the upper jaw model supporting portions 11 and the lower jaw model supporting portion 21, respectively. As is clear from FIG. 1, each of these supporting portions 11, 21 is laterally widened and rounded in periphery, provided in which periphery at predetermined angular intervals are a plurality of notched portions 76 serving as means for facilitating the grip of the supporting portions 11, 21 when the upper and the lower jaw model are mounted on the articulator 1, which will be described later in detail.

In the articulator 1 of the present invention having the above construction, it is possible to adjust in height the lower jaw model supporting portion 21 and the upper jaw model supporting portion 11 independently of one other. Further, it is also possible for the articulator 1 to move vertically the upper jaw model supporting portion 11 and the lower jaw model supporting portion 21 without any inclination relative to the upper frame 13 and the lower frame 23, respectively.

Figure 4:
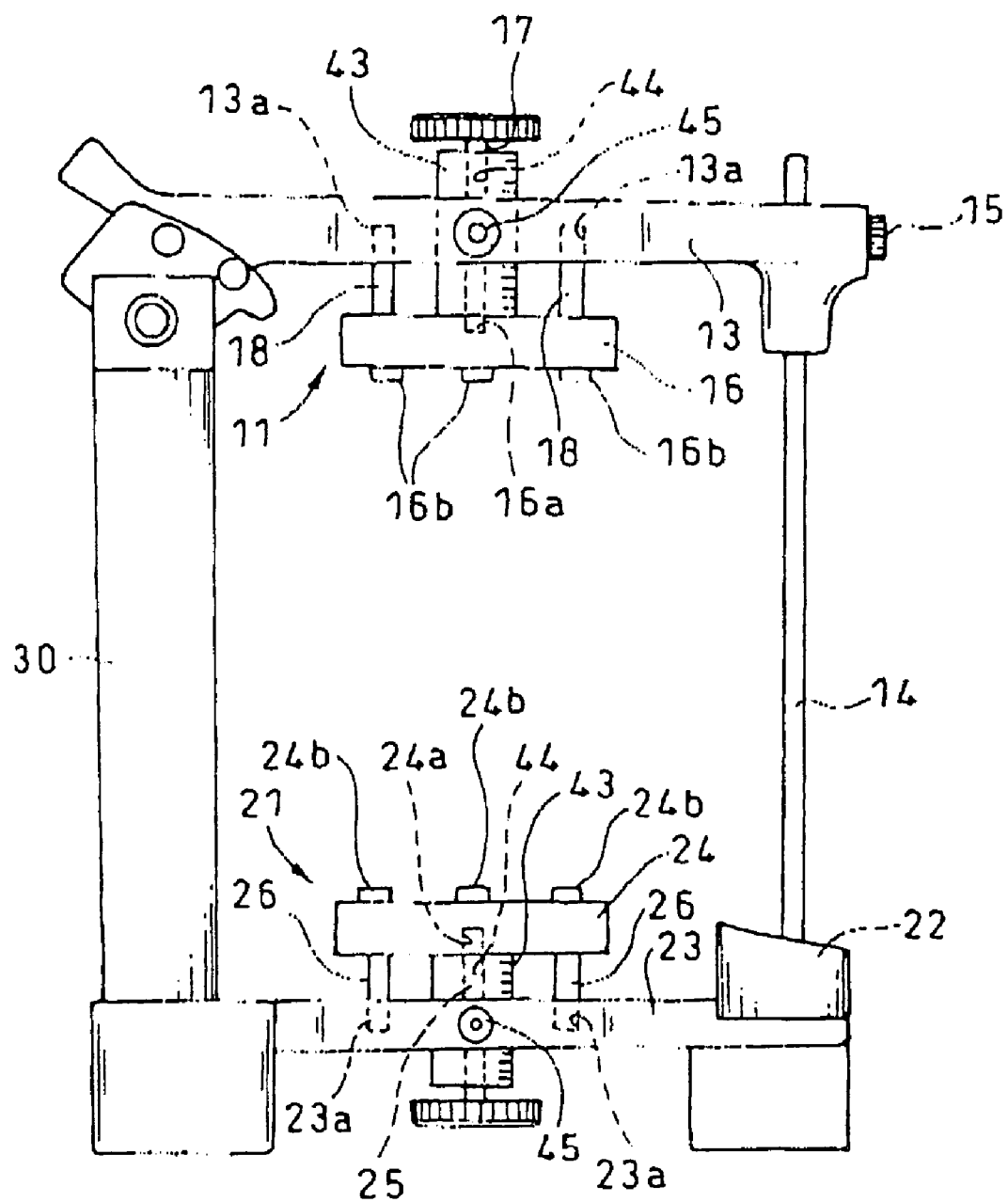
FIG. 4 is a side view of a second embodiment of the dental articulator of the present invention.

FIG. 4 shows a second embodiment of the articulator of the present invention. This second embodiment is different in construction of the height-control means from the first embodiment shown in FIGS. 1 and 2.

Incidentally, as described above in connection with the first embodiment, the height-control means of the first embodiment is constructed of the circular plate 4.

On the other hand, in the second embodiment of the articulator of the present invention, the height-control means is constructed of a calibrated cylinder 43. In the lower frame 23, as is clear from FIG. 4, such calibrated cylinder 43 is vertically slidably mounted in the lower frame 23. In other words, the calibrated cylinder 43 passes through a through-hole of the lower frame 23 from under the lower frame 23 to have its upper end portion abut on a lower surface of the circular planar stage 24.

On the other hand, in the upper frame 13, likewise, another calibrated cylinder 43 is vertically slidably mounted in the upper frame 13. In other words, the calibrated cylinder 43 passes through a through-hole of the upper frame 13 from above the upper frame 13 to have its lower end portion abut on an upper surface of the circular planar stage 16. As is clear from FIG. 4, the calibrated cylinder 43 is provided with a vertical scale in its outer peripheral surface, and has its central through-hole threaded to form a central threaded hole 44, as shown in dotted lines in FIG. 1.

In the upper frame 13, the central threaded hole 44 of the calibrated cylinder 43 receives therein the treaded portion of the stop screw 17 and is threadably engaged therewith. Likewise, in the lower frame 23, the central threaded hole 44 of the other calibrated cylinder 43 receives therein the threaded portion of the stop screw 25 and is threadably engaged therewith.

These stop screws 17 and 25 have their threaded and projected end portions threadably engaged with threaded holes 16a and 24a of the circular planar stages 16 and 24, respectively, so that the stop screws 17 and 25 are fixedly mounted on the corresponding circular planar stages 16 and 24, respectively.

On the other hand, as is clear from FIG. 4, a lateral screw member 45 is threadably engaged with a threaded through-hole (not shown) of a side portion of each of the upper frame 13 and the lower frame 23 to have its front end portion abut against a side peripheral portion of the calibrated cylinder 43. Consequently, when the lateral screw member 45 is fastened, it is possible to rigidly fix the calibrated cylinder 43 to each of the corresponding frames 13, 23. In other words, it is possible to control the calibrated cylinder 43 in its effective length in the articulator 1 by using the lateral screw member 43 without involving any inclination of each of the circular planar stages 16, 24. Due to this, it is possible for the articulator 1 to permit the circular planar stage 16 of the upper frame 13 to move vertically with out any inclination relative to the corresponding circular planar stage 24 of the lower frame 23.

As is clear from FIG. 4, the upright projections 18 and 26 are formed in the corresponding frames 13 and 23, respectively, to project inward in the articulator 1. More specifically, the corresponding frames 13 and 23 are provided with blind holes 13a and 23a, respectively. Consequently, the corresponding upright projections 18 and 26 are fixedly mounted in these blind holes 13a and 23a, respectively. It is also possible to unite these upright projections 18 and 26 with the corresponding circular planar stages 16 and 24, respectively, as is in the case of the first embodiment shown in FIGS. 1 and 2. In this case, the blind holes 13a and 23a are formed in the corresponding circular planar stages 16 and 24, respectively.

With the exception of the above construction, there is substantially no difference in construction between the first embodiment (shown in FIG. 1) and the second embodiment (shown in FIG. 4). Consequently, through these embodiments, like reference numerals or characters apply to similar parts.

As a result, in the articulator 1 of the present invention having the above construction, it is possible to readily know in position or height the circular planar stages 16, 24 relative to the corresponding frames 13, 23 by reading the scales of the calibrated cylinders 43 even when the circular planar stages 16, 24 is adjusted in height by loosing the corresponding lateral screw members 45.

The calibrated cylinder 43 may have any shape in cross section, for example such as a square shape, a triangular shape and the like. Essentially, the calibrated cylinder 43 is an elongated member capable of being fixed to the corresponding frame (13 or 23) by fastening the corresponding lateral screw members 45.

Figure 5:
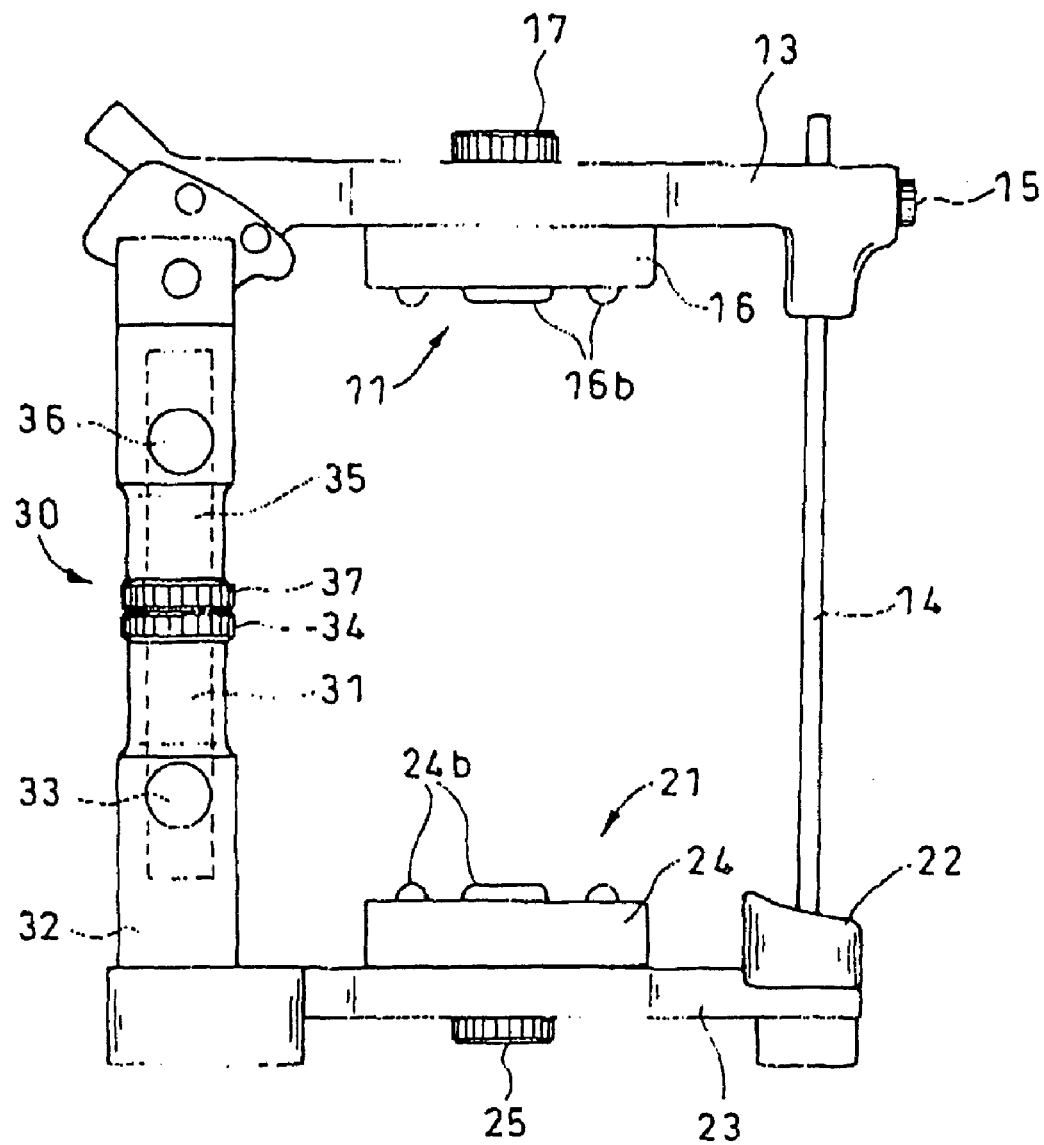
FIG. 5 is another side view of the second embodiment of the dental articulator of the present invention shown in FIG. 4.

FIG. 5 shows a third embodiment of the articulator of the present invention. A height-control means of this third embodiment is different in construction from those of the fist and the second embodiment.

In other words, in this third embodiment, as shown in FIG. 5, a pair of the stand portions 30 are disposed upright in a rear portion of the lower frame 23. Mounted on an upper surface of the lower frame 23 is the lower jaw model supporting portion 21 on which the lower jaw model 20 is detachably mounted.

In this third embodiment, the height-control means (such as the circular plates 40 in the first embodiment, and the calibrated cylinder 43 in the second embodiment) is constructed of an adjusting shaft 31. This shaft or height-control means 31 is disposed inside each of the stand portions 30 to have its lower portion and its upper portion threadably engaged with a lower stand 32 and an upper stand 35, respectively. A pair of dial members 34, 37 are threadably engaged with an intermediate threaded portion of the adjusting shaft 31. Due to this, it is possible for the dial members 34, 37 to move vertically relative to the adjusting shaft 31 when they 34, 37 are rotated relative to the shaft 31.

More specifically, when the dial member 34 disposed adjacent to an upper end portion of the lower stand 32 is rotated relative to the adjusting shaft 31, the shaft 31 is vertically moved relative to the lower stand 32. On the other hand, when the dial member 37 disposed adjacent to a lower end portion of the upper stand 35 is rotated relative to the adjusting shaft 31, the shaft 31 is vertically moved relative to the upper stand 35. Due to this, it is possible to adjust in height the upper jaw model supporting portion 16 and the lower jaw model supporting portion 21 independently of one other, whereby it is possible to move the upper jaw model 10 and the lower jaw model 20 in parallel with each other in the occlusion plate.

As shown in FIG. 5, the lower stand 32 and the upper stand 35 are provided with lateral threaded through-holes 33 and 36, respectively. When a lateral screw member (not shown) such as that 45 used in the second embodiment is threadably engaged with the threaded holes 33 and then fastened, it is possible to fix the lower stand 32 to the adjusting shaft 31. Likewise, another lateral screw member (not shown) such as that 45 used in the second embodiment is threadably engaged with the threaded holes 36 and then fastened, it is possible to fix the upper stand 35 to the adjusting shaft 31. Consequently, as is the case of the calibrated cylinder 43 used in the second embodiment shown in FIG. 4, the adjusting shaft 31 serves as the height-control means in the articulator of the present invention.

Further, in the third embodiment, as shown in FIG. 5, after completion of the height control of each of the lower stand 32 and the upper stand 35, an effective length of the incisal pin 14 is adjusted in a manner such that the upper frame 13 is disposed in parallel with the occlusion plane in a condition in which a lower end portion of the incisal pin 14 is brought into contact with an upper surface of the incisal table 22.

Consequently, in the third embodiment of the articulator having the above construction, it is possible to move the upper jaw model supporting portion 11 and the lower jaw model supporting portion 21 in parallel with each other in the occlusion plane by using the height-control means or adjusting shaft 31.

It is preferable to provide a vertical scale in an outer peripheral surface of the adjusting shaft 31 in order to facilitate the reading of the effective distance between the upper frame 13 and the lower frame 23.

Now, a process for preparing a new denture from an existing or old denture 50 by using the articulator 1 of the present invention having the above construction will be described with reference to FIGS. 6 to 14.

First of all, a pair of the old or existing dentures 50 comprising the old upper denture 51 and the old lower denture 52 are returned to a patient's mouth to determine, in consultation with the patient: an amount of height being increased in an upper old denture 51; and, an amount of height being reduced in a lower old denture 52. The thus determined amounts of height are recorded in a dental chart for the patient.

After that, it is necessary to determine in consultation with the patient whether or not the existing dentures 50 are sufficient in adherence to the patient's gum by suction, and also necessary to determine whether or not the patient wearing the existing dentures 50 has a good bite.

When the existing dentures 50 are not sufficient in adherence to the patient's gum by suction, it is necessary to explain to the patient that appropriate modification of the existing dentures 50 in shape by addition and modification of both an iso-compound or resin material 61 and an impression material 62 in each of the existing dentures 50 makes the old dentures 50 sufficient in adherence to the patient's gum by suction. The above-mentioned addition and modification of these materials 61, 62 in each of the old dentures 50 will be described later in detail with reference to FIGS. 7 and 8, and hereinafter referred to as the "myoplastic operation" of the old dentures 50.

Figure 6:
FIG. 6 is a perspective view of a silicone bite piece provided with the occlusion pattern of the old denture.

More specifically, before the myoplastic operation of the old dentures 50 is conducted, the old dentures 50 are placed in the patient's mouth. Then, a silicone-based material is loaded on each of a lower and an upper denture's teeth arch. After that, the silicone-based material is kept for approximately 60 seconds to permit the material to be set or hardened, whereby a silicone bite 55, which is a negative impression of each of the upper old denture 51 and the lower old denture 52 in occlusion arrangement, is obtained. Such negative impression or silicone bite 55 has a U-shaped form in plan view, as shown in FIG. 6.

Figure 7:
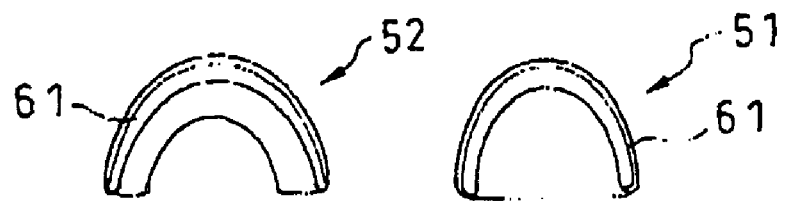
FIG. 7 is a plan view of each of the old upper denture and the old lower denture each viewed from the interior of the patient's oral cavity after completion of reproduction of the patient's tooth pattern and gum outline.

Then, as shown in FIG. 7, the iso-compound or resin material 61 is applied to a border portion of the tissue side of each of the upper old denture 51 and the lower old denture 52 to form a dam in such border portion. After the formation of the dam in the tissue side, the old dentures 50 are returned to the patient's mouth or oral cavity to have the dam of each of the old upper denture 51 and the old lower denture 52 brought into direct contact with a mucous membrane of each of the upper jaw and the lower jaw and modified thereby in shape so as to neatly fit the mucous membrane of the patient's oral cavity.

Figure 8:
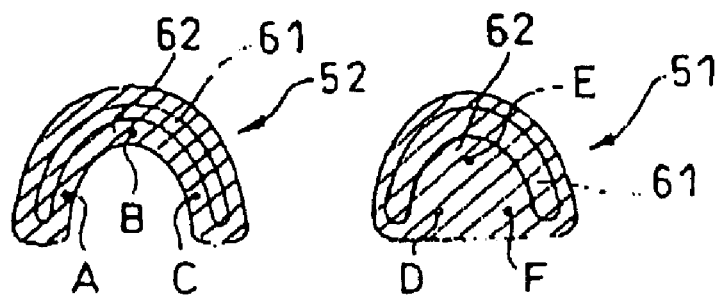
FIG. 8 is a plan view of each of the old upper denture and the old lower denture each viewed from the interior of the patient's oral cavity after completion of reproduction of the patient's tooth pattern and gum outline, illustrating the impression material applied to each of the old dentures shown in FIG. 7.

Then, as shown in FIG. 8, a sufficient amount of an impression material 62 is loaded in the tissue side of each of the old upper denture 51 and the old lower denture 52 and returned to the patient's mouth. In this case, each of the old upper denture 51 and the old lower denture 52 functions as a dental tray. As a result, the impression material 62 thus loaded in the tissue side of each of the old upper denture 51 and the old lower denture 52 is brought into contact with the entire mucous membrane of each of the patient's upper and lower jaws and modified thereby in shape so as to entirely fit each of the patient's upper and lower jaws or oral cavity. The impression material 62 thus modified in shape is shown in shaded areas in FIG. 8.

The above-mentioned modification of the impression material 62 together with the dam's formation and modification in shape in each of the old or existing dentures 50 is called the "myoplastic operation" in the art.

Next, a step for measuring each of the thus impressed old upper denture 51 and lower denture 52 in thickness in a plurality of portions thereof to determine an average thickness of each of the impressed old upper denture 51 and lower denture 52 is conducted. It is preferable to measure the thickness at least three different points, for example: points "A", "B" and "C" as to the old lower denture 52; and, points "D", "E" and "F" as to the old upper denture 51, by means of a probe which is an instrument used in the inspection of periodontosis. Further, it is also preferable to record an average of measured thickness values (which range from 0.5 mm to 3.0 mm) in the dental chart for the patient.

Figure 9:
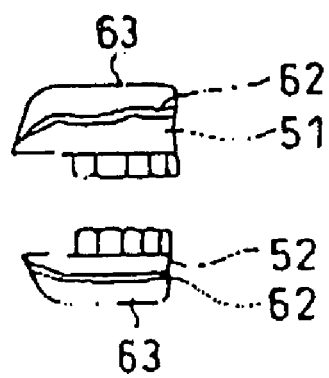
FIG. 9 is a side view of each of the old upper denture and the old lower denture both shown in FIG. 8, illustrating a gypsum material applied to the old dentures.

Then, conducted subsequent to the above denture modification step is a step for pouring a dental stone material 63 such as anhydrite or super anhydrite on an impression side of each of the thus impressed existing dentures 51, 52 to permit the dental stone material 63 to be set or hardened. As a result, as shown in FIG. 9, a dental stone negative mold (63) of each of the impressed old dentures 50 is obtained with respect to each of the upper old denture 51 and the lower old denture 52. The dental stone negative mold (63) obtained in the upper old denture 51 forms an upper jaw's oral cavity inner model. On the other hand, the dental stone negative mold obtained in the lower old denture 52 forms a lower jaw's oral cavity inner model. Each of these oral cavity inner models is a semi-finished product. Incidentally, the dental stone material (more specifically, anhydrite) 63 used in this embodiment is finer in grain size and harder in hardness than gypsum to make it possible to precisely reproduce in shape the impression material 62 having been modified in shape in the tissue side of the patient's oral cavity.

In the articulator 1 of the present invention, it is necessary to dispose the circular plate 40 (which has a thickness of 3 mm to provide a reference plane) between the circular planar stage 16 and the upper jaw model supporting portion 11 of the upper frame 13.

Figure 10:
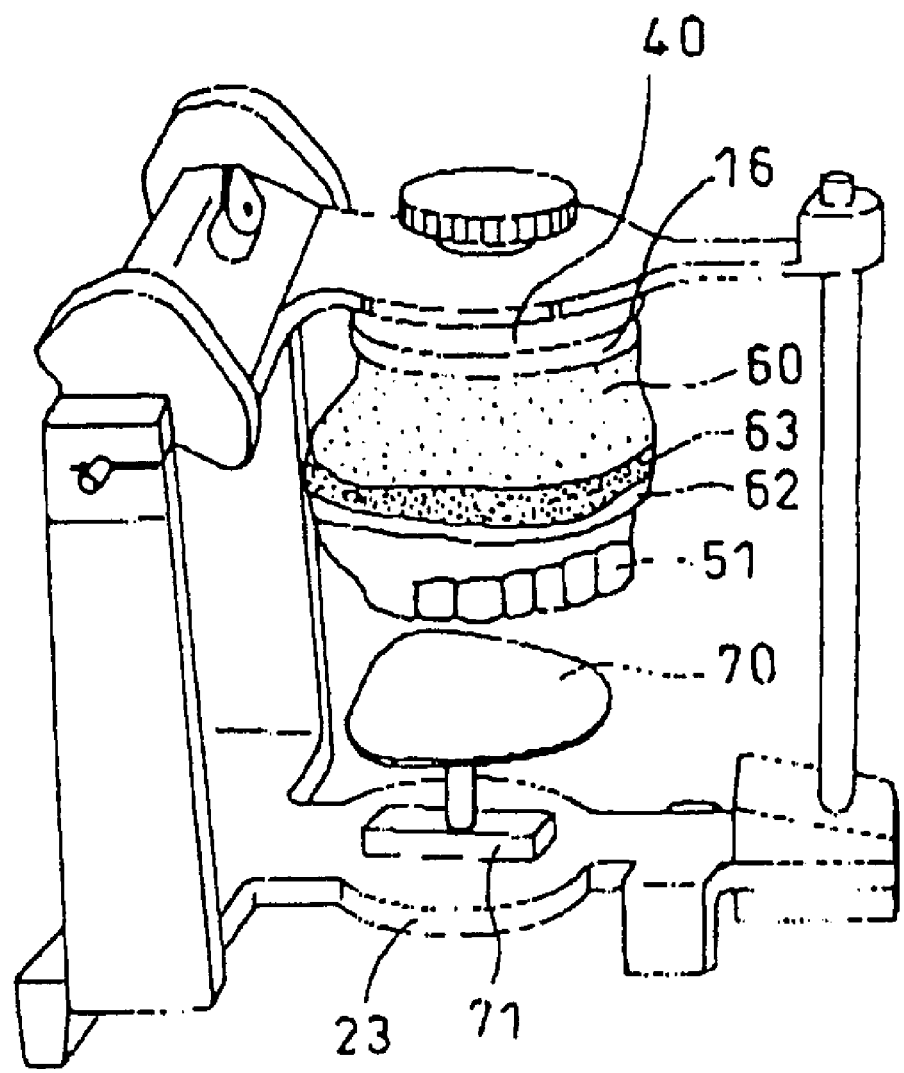
FIG. 10 is a perspective view of the dental articulator of the present invention shown in FIG. 1, illustrating the old upper denture fixedly mounted on the dental articulator.
Figure 11:
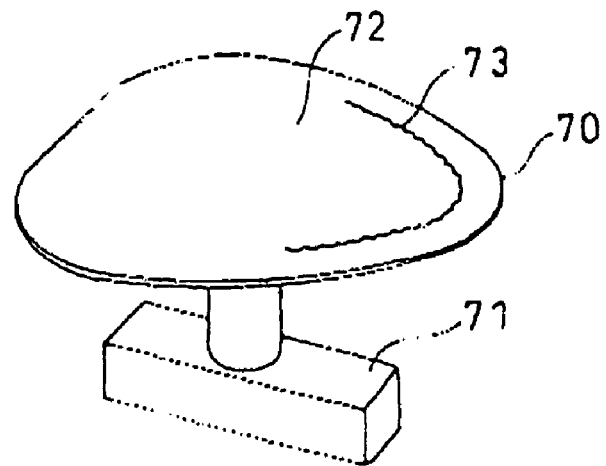
FIG. 11(A) is a perspective view a bite member mounted on the dental articulator of the present invention shown in FIG. 1, illustrating a pattern of the old upper denture's dentition arch impressed in an upper planar surface of the bite member.
FIG. 11(B) is a rear view of the bite member shown in FIG. 11(A)
Figure 11:
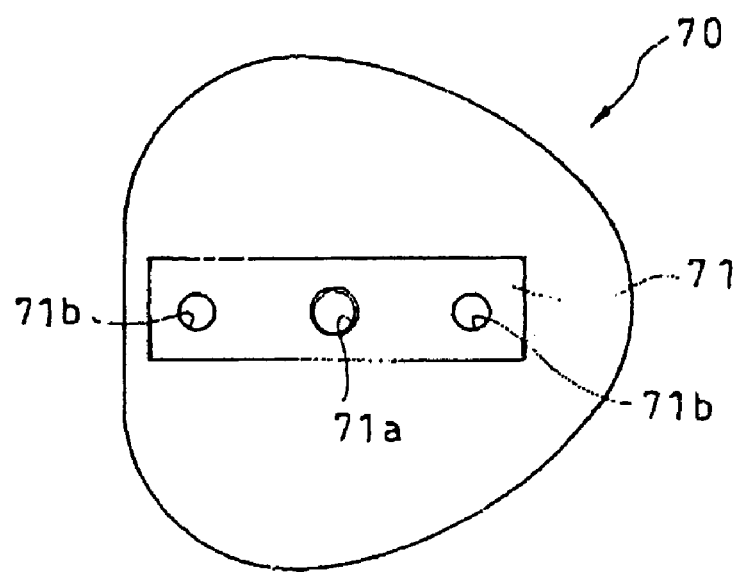
Figure 12:
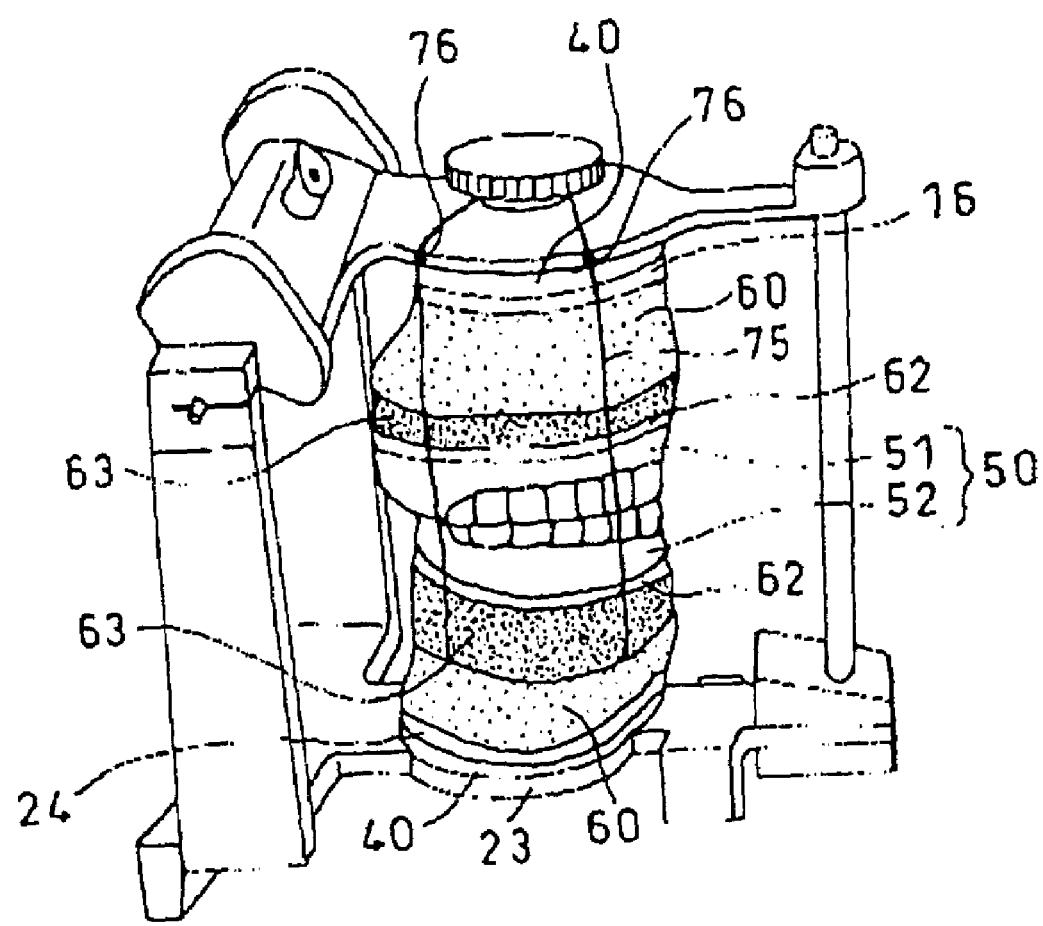
FIG. 12 is a perspective view of the dental articulator of the present invention shown in FIG. 1, illustrating the old upper denture and the old lower denture both fixedly mounted on the dental articulator.

Conducted subsequent to the above dental stone impression step is a step for mounting an occlusion planar plate 70 on the lower frame 23 of the dental articulator 1 (see FIG. 10). More specifically, the occlusion planar plate 70 is directly fixed to the lower jaw model supporting portion 21 in the lower frame 23. After that, the dental stone negative mold of the impressed upper old denture 51 is temporarily mounted on the occlusion planar plate 70 using a utility wax and has its impression side bonded to the upper jaw model supporting portion 11 by means of gypsum 60 in a condition in which the lingual side of the upper old denture 51 is aligned with a center line of the occlusion planar plate 70 and gypsum 60 is applied to both the tissue side of the old upper denture 51 and the upper jaw model supporting portion 11. As a result, as shown in FIG. 10, the old upper denture thus modified and impressed is bonded to the articulator 1. In this case, the gypsum 60 is used as a bond to the upper jaw model supporting portion 11 in the articulator 1.

The occlusion planar plate 70 is provided with a leg portion 71 in its bottom. As shown in FIG. 11(B), the leg portion 71 is provided with a pair of through-holes 71b. Slidably received in these through-holes 71b are the upright projections 26 of the lower frame 23 shown in FIG. 1. As is clear from FIG. 11(B), the leg portion 71 of the occlusion planar plate 70 is further provided with a central threaded hole 71*a* between the through-holes 71*b* thereof. The threaded portion of the stop screw 25 (shown in FIG. 1) is threadably engaged with the threaded hole 71*a* of the occlusion planar plate 70 and fastened. As a result, as shown in FIG. 10, the occlusion planar plate 70 is fixedly mounted on the lower frame 23.

Further, it is also possible to telescopically adjust in height the leg portion 71 of the occlusion planar plate 70. Due to this adjustment in height, it is possible for the occlusion planar plate 70 to have a center plane of occlusion disposed on the occlusion planar plate 70 without using the circular planar stage 24 and the circular plate 40.

After the gypsum 60 having been applied to the upper old denture 51 thus impressed has set or hardened, the utility wax having been temporarily disposed on the occlusion plate 70 is removed. Then, as shown in FIG. 11(A), an impression paper 72 is applied to an upper surface of the occlusion plate 70. Under such circumstances, an impression 73 of the dental arch of the upper old denture 51 is printed on the impression paper 72.

Next, the occlusion plate 70 is removed from the lower frame 23. After that, the circular plate 40 (which has a thickness of 3 mm, for example, and provides a reference plane) is disposed between the circular planar stage 24 and the lower jaw model supporting portion 21 of the lower frame 23 in a manner similar to disposition of the corresponding another circular plate 40 disposed between the circular planar plate 16 and the upper frame 13. Then, through the U-shaped silicone bite 55 (shown in FIG. 6) having the negative impression of the old lower denture 52, the old lower denture 52 is combined with the old upper denture 51 by using a fastening means 75, for example such as: a band such as a rubber band; a piece of wire; or, like winding means. It is preferable to have the fastening means 75 fit in each of a plurality of notched portions 76 formed in the upper fame 13 (see FIG. 1) in order to firmly combine the old dentures 50 with each other.

In a condition in which the old dentures 50 are firmly combined with each other using the fastening means 75 described above, as shown in FIG. 12, the tissue side of each of the old denture 50 including its dental stone negative molds (63) is firmly bonded to each of the corresponding circular planar stages 16, 24 by using a gypsum 60, wherein each of the stages 16, 24 is mounted on each of the upper frame 13 and the lower 23 through each of the corresponding circular plates 40.

Figure 13:
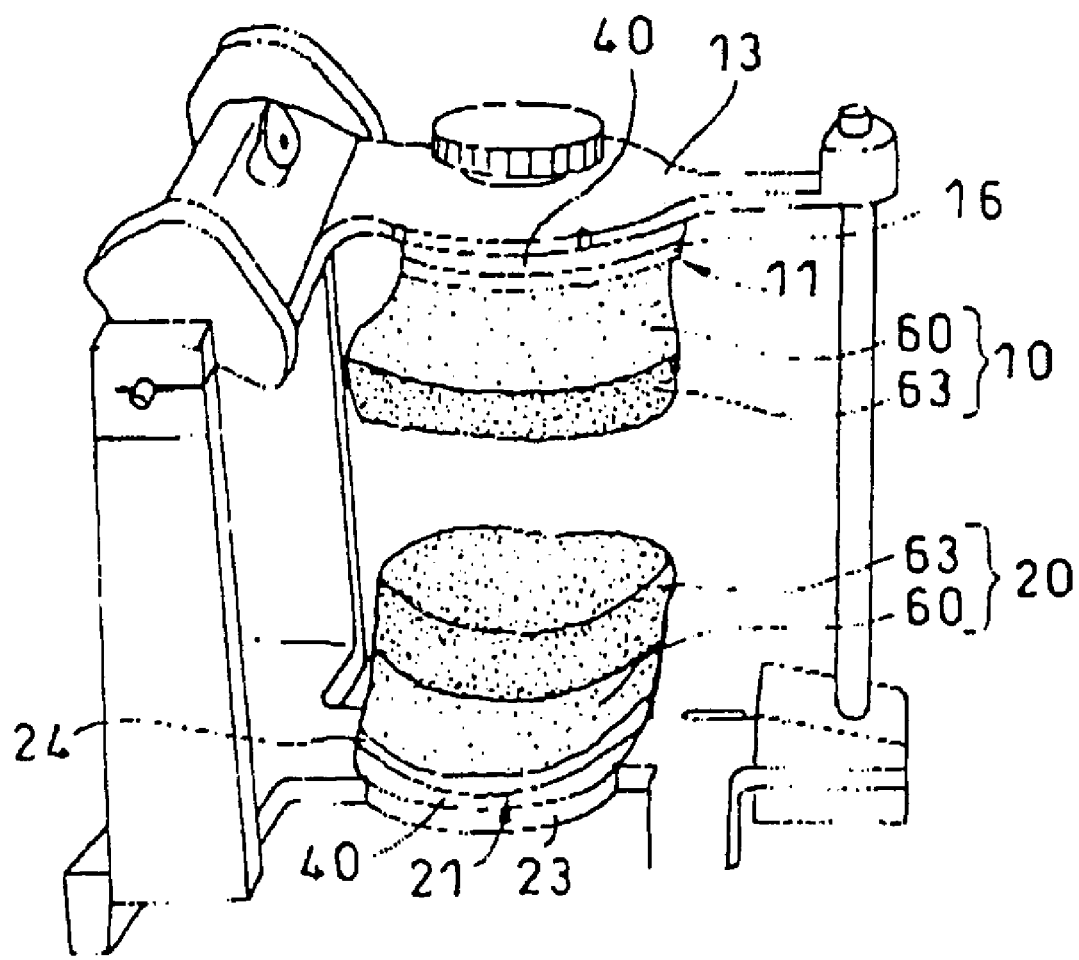
FIG. 13 is a perspective view of the dental articulator of the present invention shown in FIG. 1, illustrating the upper jaw model and the lower jaw model both formed after removal of both the old upper denture and the old lower denture.

After completion of bonding operation of the old dentures 50 to the corresponding dental stone negative molds (63) of the old dentures 50, the fastening means 75 is cut off to separate the old dentures 50 from their corresponding dental stone negative molds (63). As a result, as shown in FIG. 13, the upper jaw model 10 and the lower jaw model 20 are obtained. Each of these jaw models 10, 20 is constructed of the dental stone negative mold (63) and the gypsum 60 having been set or hardened in the above process set. After that, the old dentures 50 may be returned to the patient.

A distance between the upper jaw model 10 and the lower jaw model 20 is called as "occlusion height" in the art. The occlusion height of the jaw models 10, 20 is higher than that of the old dentures 50 by the sum of the impression materials 62 in thickness having been loaded on the old dentures 50. In other words, in case that new dentures having the same occlusion height are produced from the existing dentures 50, it is necessary to adjust in height the upper jaw model 10 and the lower jaw model 20 so as to be lower and higher than those of the corresponding old upper denture 51 and the old lower denture 52 by the thickness the corresponding upper and the lower impression material 62, respectively.

More specifically, when the impression material 62 is loaded on the tissue side of each of the old dentures 50, the average in thickness of the thus loaded and modified impression material 62 has been recorded in the dental chart for the patient, as described above. Due to this, it is possible to apply the average in thickness of the impression material 62 to such adjustment in height of the jaw models 10, 20.

Figure 14:
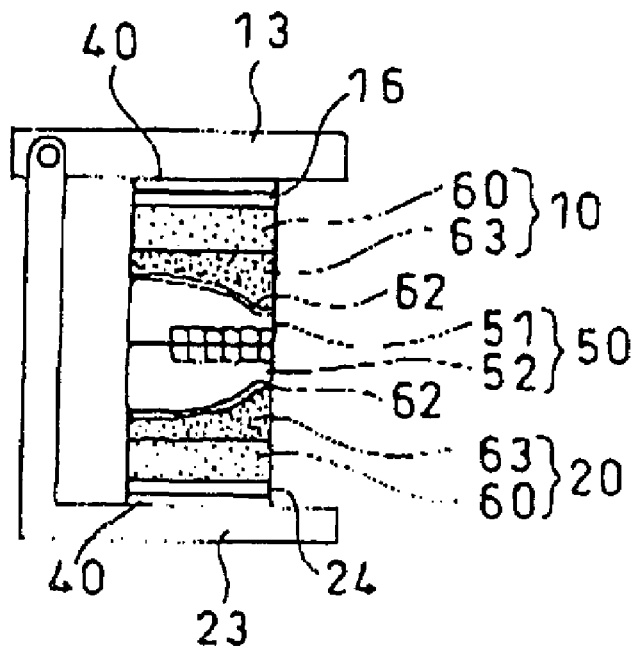
FIG. 14(a) is a side view of the dental articulator of the present invention shown in FIG. 1, illustrating the old dentures in adjusting the old dentures in occlusion height.
FIG. 14(b) is another side view of the dental articulator of the present invention shown in FIG. 1, illustrating the circular plates in adjusting the occlusion height.
Figure 14:
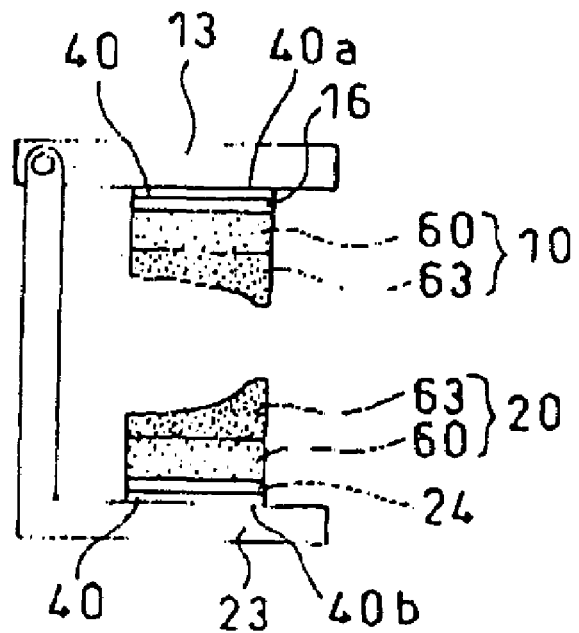

In the dental articulator 1 of the present invention having the above construction, as shown in FIGS. 14(*a*) and 14(*b*): the circular plate 40*a* is inserted between the upper frame 13 and the circular planar stage 16 to decrease the height of the upper jaw model 10, wherein the thickness of the circular plate 40*a* corresponds to the thickness of the impression material 62 loaded on the old upper denture 51; and, the circular plate 40*b* is inserted between the lower frame 23 and the circular planar stage 24 to increase the height of the lower jaw model 20, wherein the thickness of the circular plate 40*b* corresponds to the thickness of the impression material 62 loaded on the old lower denture 52.

Consequently, in the articulator 1 of the present invention, it is possible to precisely reproduce the occlusion height of the old dentures 50 by using: a first circular plate 40 providing the reference plane; and/or another circular plate 40 different in thickness from the first circular plate 40.

Further, at this time, a thickness of the circular plate 40 used in the articulator 1 of the present invention is determined in consideration of: deterioration in mastication due to a wearing down of teeth of the old dentures 50; incorrect pronunciation due to such wearing down of the teeth; aged look due to the wearing down of the teeth; and, other pieces of information. In other words, it is possible to determine an optimum value in occlusion height of the new dentures by adjusting a height of each of the new dentures on the basis of the patient's chart having been previously recorded and the patient own selection in feeling.

Incidentally, in the dental articulator 1 provided with an upper and a lower one of the circular plates 40 (each providing a reference plane and a thickness of 3 mm, for example), in order to increase the occlusion height, it suffices to replace these circular plates 40 with new circular plates 40 each having a thickness of less than 3 mm. For example, each of the new circular plates 40 may have a thickness of 2 mm.

In the dental articulator 1 shown in FIG. 14(*a*), the lower jaw models 20 are first dismounted from the articulator 1. After that, an occlusion plate 70 is mounted on the lower frame 23 of the articulator 1. Then, a paraffin wax is applied to the upper jaw model 10, so that teeth of a new upper denture are arranged with reference to the impression 73 of the dental arch of the upper old denture 51 printed on the impression paper 72 mounted on the occlusion plate 70.

After that, the occlusion plate 70 is dismounted from the lower frame 23 of the articulator 1. Then, the lower jaw models 20 are mounted on the lower frame 23 of the articulator 1. After that, a paraffin wax is applied to the lower jaw model 20. Then, teeth of a new lower denture are properly arranged so as to be properly engaged with the corresponding teeth of the new upper denture, so that an upper and a lower occlusion dam in a border portion of the existing dentures are completed, wherein the dam formed in the border portion of each of the existing dentures is brought into contact with a mucous membrane of a patient's oral cavity and thereby modified in shape by the contact with the mucous membrane to fit the the oral cavity, wherein the existing dentures provided with the dams thus formed and modified in shape in the border portions thereof are referred to as the modified existing dentures.

Based on the occlusion dams thus formed in the above, the new dentures are produced after negative impressions are produced through a conventional implantation process.

In the dental articulator 1 of each of the above-mentioned embodiments, there is provided the height-control means (40, 43, 31). Due to such provision of the height-control means, each of the upper and the lower upper jaw model supporting portions (11 and 21, respectively) is capable of moving to a new position parallel to itself in each of the corresponding upper and the lower frame (13 and 23, respectively).

Figure 15:
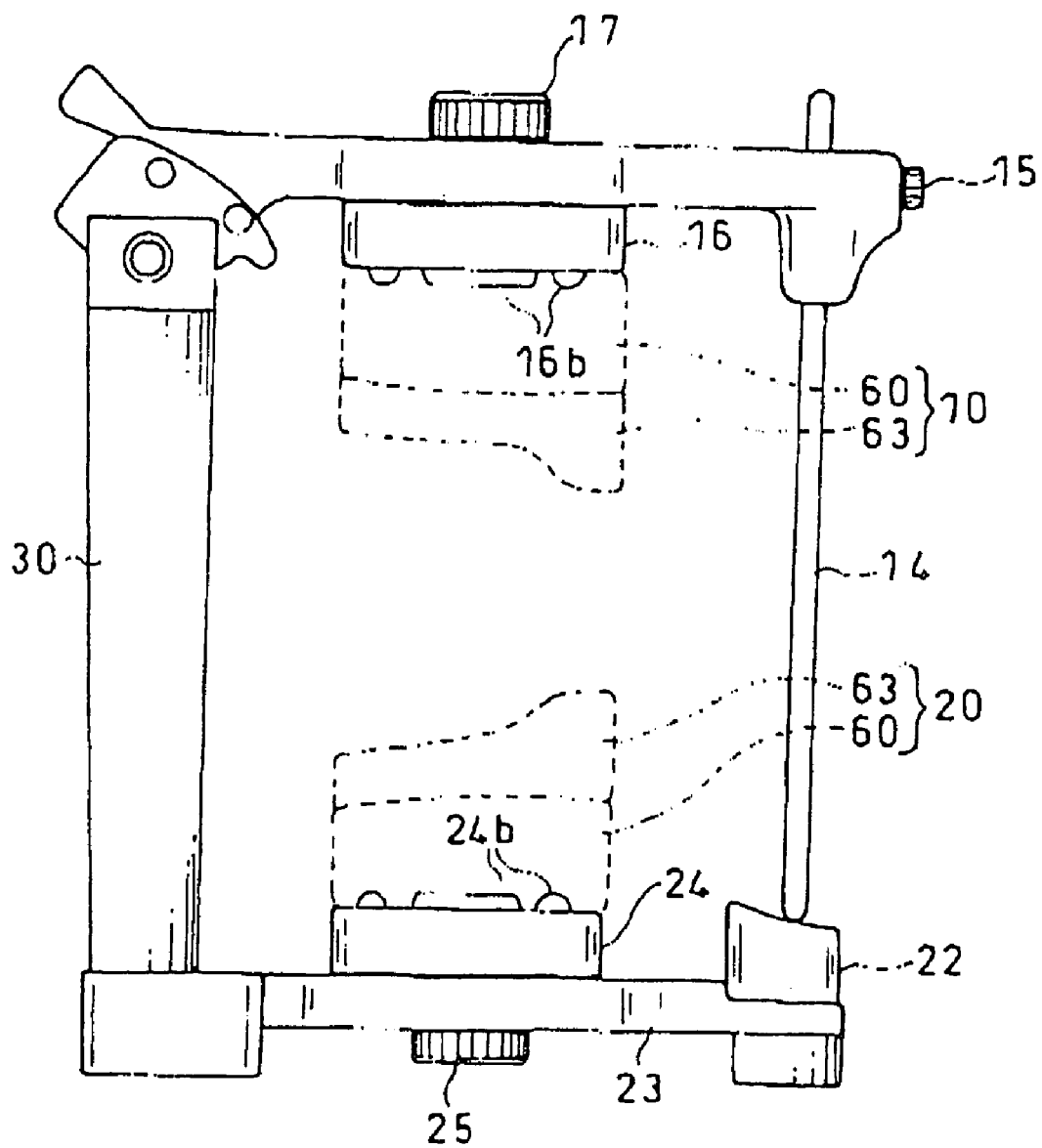
FIG. 15 is a side view of the second embodiment of the dental articulator shown in FIG. 5 in a condition in which the old dentures are removed from the articulator.
Figure 15:
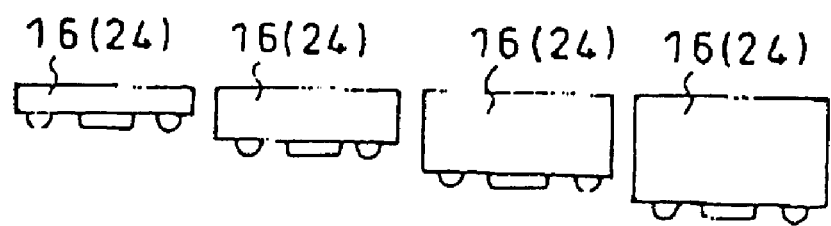
Figure 16:
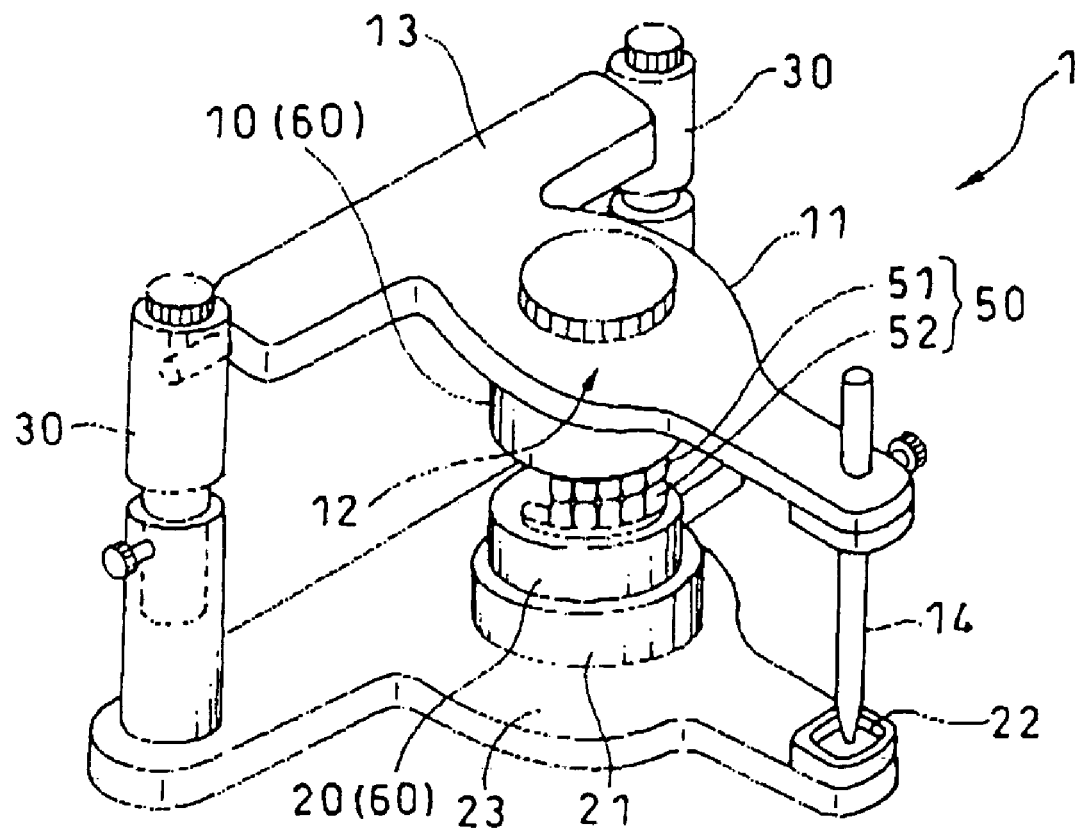
FIG. 16 is a perspective view of the conventional dental articulator, illustrating its basic construction.

On the other hand, there is another type of the height-control means, as shown in FIG. 15. Namely, as shown in FIG. 5, this type of height-control means is constructed of a plurality of circular planar stages 16, 24 which differ from each other in thickness. In use, a first one of the circular planar stages 16, which one has a first thickness, is mounted on the upper jaw model supporting portion 11 of the upper frame 13. In adjusting the occlusion height of the articulator 1, the first one of the circular planar stages 16 is replaced with a second one of the circular planar stage 16 having a second thickness, so that the occlusion height of the articulator 1 is adjusted. It is also possible to adjust the occlusion height of the articulator 1 by replacing a first one of the circular planar plates 24 with a second one different in thickness from the first one in the lower jaw model supporting portion 21 of the lower frame 23, provided that the circular planar stages 16, 24 are capable of moving parallel to the corresponding frames 23, 13 in the articulator 1.

As is clear from the above description, in order to adjust the occlusion height in the embodiment shown in FIG. 15, it is necessary to replace the circular planar stages 16, 24. Due to this, it is preferable to apply a suitable release agent to each of an upper surface of the lower circular planar stage 24 and a lower surface of the upper circular planar stage 16 in order to facilitate separation of the lower jaw model 20 and the upper jaw model 10 from the corresponding lower circular planar stage 24 and the upper circular planar stage 16, respectively, wherein the lower jaw model 20 and the upper jaw model 10 are made of gypsum on the corresponding lower circular planar stage 24 and the upper circular planar stage 16, respectively.

In FIG. 15, the remaining parts, which are the same as ones in FIG. 1, have been given the same reference numerals used in FIG. 1, and therefore not further explained here.

As is clear from the above description, since the articulator 1 of the present invention having the above construction is provided with the height-control means (40, 43, 31), it is possible to adjust in height each of the upper and the lower jaw model (10 and 20, respectively) relative to the corresponding lower and the upper frame (23 and 13, respectively), respectively, so as to be moved to a new position parallel to itself. Consequently, the articulator 1 of the present invention is capable of precisely reproducing the optimum occlusion height of the patient's oral cavity without fail.

Further, in production of the new dentures by using the articulator 1 of the present invention, it is possible to adjust in horizontal position both the upper and the lower jaw model in the articulator 1 independently of each other in an easy manner. Due to this, it is possible to find an appropriate position of each of the upper and the lower jaw model corresponding the above optimum occlusion height of the patient's oral cavity. Still further, in the articulator 1 of the present invention, it is possible to produce the most-suitable new dentures from the existing dentures by utilizing the information of the existing dentures effectively.

In the method of the present invention for adjusting the occlusion height in preparing the new denture from the existing dentures by using the dental articulator 1 provided with the height-control means (i.e., a mechanism for adjusting the occlusion height defined between the upper jaw model supporting portion and the lower jaw model supporting portion), these supporting portions are adjustable in height independently of each other, and the upper jaw model and the lower jaw model are detachably mounted on the upper jaw model supporting portion and the lower jaw model supporting portion, respectively.

This method of the present invention comprises the steps of:

forming and modifying in shape a dam in a border portion of said existing denture, wherein said dam formed in said border portion of said existing denture is brought into contact with a mucous membrane of a patient's oral cavity and thereby modified in shape by the contact with said mucous membrane so as to fit said membrane, wherein the existing denture provided with said dam thus formed and modified in shape in said border portion is referred to as the modified existing denture;

loading an impression material in a tissue side of said modified existing denture, wherein said impression material thus loaded is brought into detachable contact with said mucous membrane of the patient's oral cavity by the insertion in said oral cavity of said modified existing denture having been loaded with said impression material to obtain the impression of said oral cavity in said impression material of said modified existing denture, wherein said modified existing denture provided with the impression of said oral cavity is referred to as the impressed existing denture;

measuring said impressed existing denture in thickness in a plurality of portions thereof to determine an average thickness of said impressed existing denture;

pouring gypsum on an impression side of said impressed existing denture to permit said gypsum to be set or hardened, so that a dental stone negative mold of said impressed existing denture is obtained with respect to each of an upper and a lower existing denture;

mounting an occlusion planar plate (70) on the dental articulator (1), wherein said dental stone negative mold of said impressed upper existing denture is temporarily mounted on said occlusion planar plate (70) and has its impression side bonded to said upper jaw model supporting portion (11) by means of gypsum;

dismounting said occlusion planer plate (70) from said dental articulator (1), wherein said impressed upper existing denture having been bonded to said upper jaw model supporting portion (11) is mated with the corresponding impressed lower existing denture to form them into a single unit by means of a band, wherein said single unit has the impression side of its impressed lower existing denture bonded to said lower jaw model supporting portion (21);

dismounting said impressed upper existing denture from said upper jaw model supporting portion (11) to form an upper dental stone negative mold of said upper impressed existing denture, wherein said impressed lower existing denture is dismounted from said lower jaw model supporting portion (23) to form a lower dental stone negative mold of said lower jaw model supporting portion (23); and adjusting the occlusion height with reference to said average thickness of said impressed existing denture, wherein the adjustment is conducted by adjusting in level said upper jaw model supporting portion (11) and said lower jaw model supporting portion (21) independently of each other.

As for the method of the present invention described above, in the step of dismounting the occlusion planer plate (70) from the articulator (1), the impressed upper existing denture having been bonded to the upper jaw model supporting portion (11) is mated with the corresponding impressed lower existing denture to form them into a single unit by means of a band, wherein the single unit has the impression side of its impressed lower existing denture bonded to the lower jaw model supporting portion (21).

Conducted subsequent to the above step is a step for dismounting the impressed upper existing denture 51 from the upper jaw model supporting portion 11 to form an upper dental stone negative mold of the upper impressed existing denture, wherein the impressed lower existing denture 52 is dismounted from the lower jaw model supporting portion 23 to form a lower dental stone negative mold of the lower jaw model supporting portion 23.

Conducted subsequent to the above step is a step for adjusting the occlusion height with reference to the average thickness of each of the impressed existing dentures 51, 52, wherein the adjustment is conducted by adjusting in level the upper jaw model supporting portion 1 and the lower jaw model supporting portion 21 independently of each other.

Incidentally, after removal of the occlusion plate 70, the circular plate 40 having a thickness of 3 mm is interposed between the lower jaw model supporting portion 21 and the lower frame 23, wherein the circular plate 40 serves as a reference plane.

In a method of the present invention for adjusting an occlusion height in preparing a new denture from the existing one by using the articulator 1 provided with a mechanism for adjusting the occlusion height defined between the upper jaw model supporting portion 11 and the lower jaw model supporting portion 21, wherein these supporting portions 11, 21 are adjustable in height independently of each other, and the upper jaw model 10 and the lower jaw model 20 are detachably mounted on the upper jaw model supporting portion 11 and the lower jaw model supporting portion 21, respectively, the method comprises the steps of:

forming and modifying in shape a dam in a border portion of the existing denture, wherein the dam formed in the border portion of the existing denture is brought into contact with a mucous membrane of a patient's oral cavity and thereby modified in shape by the contact with the mucous membrane so as to fit the said oral cavity, wherein the existing denture provided with the dam thus formed and modified in shape in the border portion thereof is referred to as the modified existing denture;

loading an impression material in a tissue side of the modified existing denture, wherein the impression material thus loaded is brought into detachable contact with the mucous membrane of the patient's oral cavity by the insertion in the oral cavity of the modified existing denture having been loaded with the impression material to obtain the impression of the oral cavity in the impression material of the modified existing denture, wherein the modified existing denture provided with the impression of the oral cavity is referred to as the impressed existing denture;

measuring the impressed existing denture in thickness in a plurality of portions thereof to determine an average thickness of the impressed existing denture;

pouring gypsum on an impression side of the impressed existing denture to permit the gypsum to be set or hardened, so that a dental stone negative mold of the impressed existing denture is obtained with respect to each of an upper and a lower existing denture;

mounting an occlusion planar plate 70 on the dental articulator 1, wherein the dental stone negative mold of the impressed upper existing denture is temporarily mounted on the occlusion planar plate 70 and has its impression side bonded to the upper jaw model supporting portion 11 by means of gypsum;

dismounting the occlusion planer plate 70 from the dental articulator 1, wherein the impressed upper existing denture having been bonded to the upper jaw model supporting portion 11 is mated with the corresponding impressed lower existing denture to form them into a single unit by means of a band, wherein the single unit has the impression side of its impressed lower existing denture bonded to the lower jaw model supporting portion 21;

dismounting the impressed upper existing denture from the upper jaw model supporting portion 11 to form an upper dental stone negative mold of the upper impressed existing denture, wherein the impressed lower existing denture is dismounted from the lower jaw model supporting portion 23 to form a lower dental stone negative mold of the lower jaw model supporting portion 23; and adjusting the occlusion height with reference to the average thickness of the impressed existing denture, wherein the adjustment is conducted by adjusting in level the upper jaw model supporting portion 11 and the lower jaw model supporting portion 21 independently of each other.

In effect, the articulator 1 of the present invention is characterized by the provision of the height-control means which is capable of adjusting in height the lower jaw model and the upper jaw model independently of one other without causing any inclination of these models.

In preparing the new denture from the old or existing denture, since it is possible for the dental articulator of the present invention to readily adjust the horizontal position of each of the upper jaw model and the lower jaw model independently of each other, it is possible to readily determine the position of each of the upper jaw model and the lower jaw model in accordance with individual occlusion height. Further, it is also possible for the dental articulator of the present invention to utilize information such as dentition arch's information and like information of the old denture in preparing precisely a new comfortable denture in an easy manner.

Finally, the present application claims the Convention Priority based on Japanese Patent Application No. 2002-280015 filed on Sep. 25, 2002, which is herein incorporated by reference.

What is claimed is:

1. A dental articulator comprising:
a lower frame (23) provided with a lower jaw model supporting portion (21) in its upper surface, wherein a lower jaw model (20) is detachably mounted on said supporting portion (21) through one of height-control means (16, 24, 40, 43);
a stand portion (30) disposed upright in a rear portion of said lower frame (23);
an upper frame (13) capable of performing its opening and closing motion relative to said stand portion (30), wherein said upper frame (13) is provided with an upper jaw model supporting portion (11) in its lower surface, wherein an upper jaw model (10) is detachably mounted on said supporting portion (11) through another one of said height-control means (16, 24, 40, 43);

wherein said height-control means (16, 24, 40, 43) enables said jaw model (10, 20) to be displaced vertically without any inclination relative to said frame (13, 23) and, wherein said height-control means (16, 24, 40, 43) is constructed of a plurality of circular planar stages (16, 24) which differ from each other in thickness and detachably mounted on said supporting portion (11,21) to make it possible to displace said jaw model (10, 20) vertically without any inclination relative to said frame (13, 23) when a first one of said circular planar stages (24) is exchanged for another one different from said first one in thickness.

2. A dental articulator comprising:

a lower frame (23) provided with a lower jaw model supporting portion (21) in its upper surface, wherein a lower jaw model (20) is detachably mounted on said supporting portion (21) through one of height-control means (16, 24, 40, 43);

a stand portion (30) disposed upright in a rear portion of said lower frame (23);

an upper frame (13) capable of performing its opening and closing motion relative to said stand portion (30), wherein said upper frame (13) is provided with an upper jaw model supporting portion (11) in its lower surface, wherein an upper jaw model (10) is detachably mounted on said supporting portion (11) through another one of said height-control means (16, 24, 40, 43);

wherein said height-control means (16, 24, 40, 43) enables said jaw model (10, 20) to be displaced vertically without any inclination relative to said frame (13, 23) and, wherein said height-control means (16, 24, 40, 43) is constructed of a plurality of circular plates (40) each disposed between said supporting portion (11, 21) and said circular planar stage (24) and differs from each other in thickness to make it possible to displace said jaw model (10, 20) vertically without any inclination relative to said frame (13, 23) when a first one of said circular plates (40) is exchanged for another one having a thickness different from that of said first one.

3. A dental articulator comprising:

a lower frame (23) provided with a lower jaw model supporting portion (21) in its upper surface, wherein a lower jaw model (20) is detachably mounted on said supporting portion (21) through one of height-control means (16, 24, 40, 43);

a stand portion (30) disposed upright in a rear portion of said lower frame (23);

an upper frame (13) capable of performing its opening and closing motion relative to said stand portion (30), wherein said upper frame (13) is provided with an upper jaw model supporting portion (11) in its lower surface, wherein an upper jaw model (10) is detachably mounted on said supporting portion (11) through another one of said height-control means (16, 24, 40, 43);

wherein said height-control means (16, 24, 40, 43) enables said jaw model (10, 20) to be displaced vertically without any inclination relative to said frame (13, 23) and, wherein said height-control means (16, 24, 40, 43) is constructed of a calibrated cylinder (43), said calibrated cylinder (43) passing through a through-hole of at least one of said supporting portions (11, 21) to have its front end portion abut on a circular planar stage (16, 24) 50 that said circular planar stage (16, 24) is vertically displaced without any inclination relative to said at least one of said supporting portions (11, 21) when said calibrated cylinder (43) is vertically slidably moved in said through-hole of said at least one of said supporting portions (11,21).

4. A dental articulator comprising:

a lower frame (23) provided with a lower jaw model supporting portion (21) in its upper surface, wherein a lower jaw model (20) is detachably mounted on said supporting portion (21) through one of height-control means (16, 24, 40, 43); a stand portion (30) disposed upright in a rear portion of said lower frame (23);

an upper frame (13) capable of performing its opening and closing motion relative to said stand portion (30), wherein said upper frame (13) is provided with an upper jaw model supporting portion (11) in its lower surface, wherein an upper jaw model (10) is detachably mounted on said supporting portion (11) through another one of said height-control means (16, 24, 40, 43);

wherein said height-control means (16, 24, 40, 43) is constructed of a calibrated cylinder (43) and enables said jaw model (10, 20) to be displaced vertically without any inclination relative to said frame (13, 23), wherein said calibrated cylinder (43) is provided with a vertical scale in its outer peripheral surface and a central threaded hole (44) in its central portion, which threaded hole (44) is threadably engaged with a treaded portion of a stop screw (17, 25), which threaded portion of said stop screw (17, 25) has its front end portion threadably engaged with a threaded hole (16a, 24a) of said circular planar stage (16, 24), wherein a lateral screw member (45) is threadably engaged with a threaded through-hole of a side portion of said frame (13, 23) to have its front end portion abut against a side peripheral portion of said calibrated cylinder (43) to fix the same (43) to said frame (13, 23) after said calibrated cylinder (43) is displaced by a desired amount relative to said frame (13, 23).

* * * * *